United States Patent
Yan et al.

(10) Patent No.: US 8,927,268 B2
(45) Date of Patent: Jan. 6, 2015

(54) RAPID MEMBRANE ISOLATION METHOD FOR ANIMAL AND PLANT SAMPLES

(71) Applicants: Lin Yan, Eden Prairie, MN (US); Quanzhi Li, New Brighton, MN (US)

(72) Inventors: Lin Yan, Eden Prairie, MN (US); Quanzhi Li, New Brighton, MN (US)

(73) Assignee: Invent Biotechnologies, Inc., Eden Praire, MN (US)

( * ) Notice: Subject to any disclaimer, the term of this patent is extended or adjusted under 35 U.S.C. 154(b) by 0 days.

(21) Appl. No.: 13/767,655

(22) Filed: Feb. 14, 2013

(65) Prior Publication Data
US 2013/0217114 A1 Aug. 22, 2013

Related U.S. Application Data

(60) Provisional application No. 61/600,116, filed on Feb. 17, 2012.

(51) Int. Cl.
 *C12M 1/33* (2006.01)
 *C12N 5/00* (2006.01)
 *C12M 1/00* (2006.01)

(52) U.S. Cl.
 CPC ............ *C12N 5/0006* (2013.01); *C12M 47/06* (2013.01)
 USPC ...................................... 435/306.1

(58) Field of Classification Search
None
See application file for complete search history.

(56) References Cited

U.S. PATENT DOCUMENTS 4,146,501 A * 3/1979 Henkin .................. 436/503

OTHER PUBLICATIONS

Freitas Jr. Nanomedicine, vol. I: Basice Capabilities pp. 1-2, 1999.*
"Mem-PER Eukaryotic Membrane Protein Extraction Kit" [online]. Thermo Fisher Scientific Inc., Rockford, IL, Copyright 2013 [retrieved on May 30, 2013]. Retrieved from the Internet: http://www.piercenet.com/browse/cfm?FIdID=06010422; 3 pgs.
"Plasma Membrane Protein Extraction Kit" Protocol Booklet [online]. abcam, Cambridge, MA, Copyright 1998-2013 [retrieved May 30, 2013], Retrieved from the Internet: http://www.abcam.com/ps/products/65/ab65400/documents.ab65400%20Plasma%20Membrane%20Protein%20Extraction%20Kit%20Protocol%20(website).pdf; 12 pgs.
"Plasma Membrane Protein Extraction Kit" [online]. Bio Vision Research Products, Mountain View, CA, Revised Apr. 2010 [retrieved May 30, 2013]. Retrieved from the Internet: http://www.biovision.com/manuals/K268-50.pdf; 1 pg.
"Protein Sample Preparation: Protein Extraction" [online]. EMD Millipore Corporation, Billerica, MA, Copyright 2013 [retrieved on May 30, 2013]. Retrieved from the Internet: http://www.millipore.com/lab_filtration/flx4/psp_extraction; 2 pgs.
Schimmel et al., "Plasma Membranes from Cultured Muscle Cells: Isolation Procedure and Separation of Putative Plasma-Membrane Marker Enzymes," *Proc. Nat. Acad.*, Nov. 1973, 70(11): 3195-3199.

* cited by examiner

*Primary Examiner* — Albert Navarro
(74) *Attorney, Agent, or Firm* — Mueting, Raasch & Gebhardt, P.A.

(57) ABSTRACT

Disclosed herein are methods for quickly obtaining crude membranes from cells, including animal and plant cells. The methods include incubating cells in a buffer and forcing the cells through a filter that causes rupture of the cells, and then separating the resulting crude membranes from most cytosolic proteins.

6 Claims, 3 Drawing Sheets

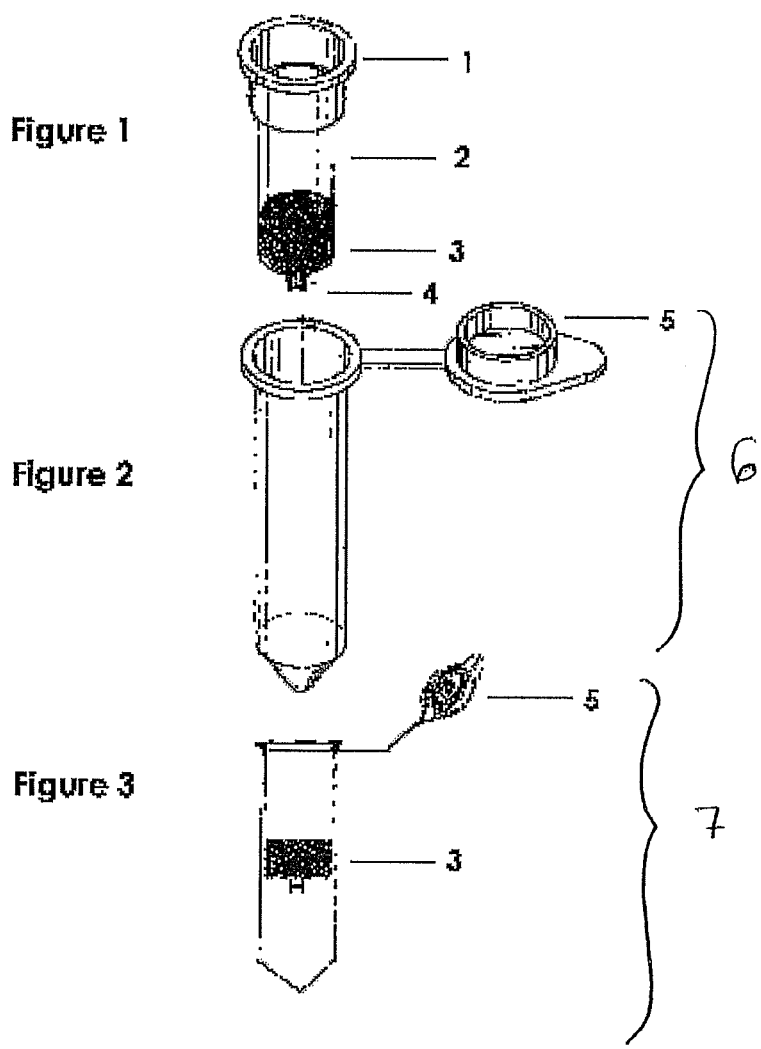

T = total cell lysate   C = cytosol fraction   M = membrane fraction

RAPID MEMBRANE ISOLATION METHOD FOR ANIMAL AND PLANT SAMPLES

CROSS-REFERENCE TO RELATED APPLICATIONS

This application claims the benefit of U.S. Provisional Application Ser. No. 61/600,116, filed Feb. 17, 2012, which is incorporated by reference herein.

BACKGROUND

Isolation of crude membranes from animal and plant cells and/or tissues is the first step for further purification and characterization of membrane and organelle proteins. Over 70% of drug targets and biomarkers are found on plasma membranes, therefore isolation and purification of membrane proteins is one of the most commonly employed procedures in biomedical research. Traditional membrane and organelle isolation protocols often involve homogenizing cultured cells and/or tissues in a hypotonic buffer or a buffer containing detergents such as Triton-X 114. The cells and/or tissues are homogenized with a glass homogenizer (such as Dounce homogenizer), sonication or a tissue blender to break up cells and/or tissues. Insoluble membrane and organelles are separated from nuclei and other soluble proteins by differential centrifugations. The procedures are tedious and time consuming; a typical procedure takes more than one hour to complete.

Several commercial kits are available for isolation of membrane proteins. These commercial kits can be roughly classified into two categories based on mechanisms of cell membrane disruption: 1) membrane protein isolation using detergents (for instance, Mem-PER Eukaryotic Membrane Protein Extraction Kit, Pierce, Rockford, Ill.) without using a glass homogenizer and 2) membrane protein isolation using a glass homogenizer (for instance, Plasma Membrane Protein Extraction Kit, Biovison, Mountain View, Calif.), and Plasma Membrane Protein Extraction Kit, abcam, Cambridge, Mass.) or a blender (for instance, Cytosolic and Nuclear Membrane Protein Extraction Protocols, Millipore, Billerica, Mass.) without using detergents.

Methods employing detergents for membrane protein isolation offer the advantages of using smaller amounts of starting cells (at least $5\times10^6$ cells) and selectively extracting certain fractions of membrane proteins; however these methods potentially alter the normal configuration of membrane and membrane proteins. Methods using glass homogenizers or blenders for membrane disruption isolate membrane proteins and organelles in their native forms and retain full protein activities. These methods generally require larger amount of starting cells ($5\times10^6$ and up). The use of glass homogenizer and tissue blenders is generally less user friendly for multiple samples and are time consuming Thorough cleaning of the homogenizer is required for each sample and there is a possibility of sample cross-contamination. Currently available commercial kits for membrane and organelle isolation are relatively tedious and time consuming. In addition to the use of glass homogenizers or tissue blenders, multiple incubation and centrifugation steps are common. These procedures usually take more than one hour to complete. A typical crude membrane isolation protocol in a research laboratory usually requires the following steps: collect cells by low speed centrifugation; wash cells and resuspend in a homogenization buffer with 0.25 M sucrose; break cells in a Dounce homogenizer and check under a phase contract microscope to determine if majority of cells are broken; centrifuge homogenate for 10 minutes at 1700×g; transfer supernatant to a new tube and centrifuge at 33,000×g for 60 minutes; and remove the supernatant leaving a pellet containing crude membranes that include plasma membrane and organelle membranes (Schimmel D. S. et al. (1973). Proc. Nat. Acad. Sci. USA, Vol. 70, pp-3195-3199).

SUMMARY OF THE APPLICATION

Provided herein are methods for facilitating isolation and subsequent analysis of membrane and/or organelle proteins from animal or plant samples through the use of membrane extraction filter cartridges. In one embodiment, the membrane extraction filter cartridge may include a hydrophobic porous material (thickness>0.1 mm) with an average pore size of 30 µm (ranging from 20-60 µm) and a molded cylinder to hold the filter in place. In one embodiment, the filter is one that is typically used for venting and gas (e.g., air) filtration. In one embodiment, the filter is a surface filter (e.g., a filter that traps certain cellular components on its surface). In one embodiment, the filter is a depth filter (e.g., a filter that is a bead of material that retains certain cellular components as they pass through it). The cellular components may include aggregated cells and/or tissue debris. Upon application of positive (such as centrifugation) or negative force (such as vacuum suction), the mixture of biological samples are forced to pass through the filter, resulting in two separated parts: retentate (on the surface and inside of the filter), and filtrate (passing through the filter).

In one embodiment, the cells are incubated with a hypotonic buffer to make cells sensitive to mechanical disruption. After incubation, swollen cells are transferred to membrane extraction filter cartridge(s) indicated in the drawings (FIG. 1-3) which is subject to a positive or negative force, such as 30 seconds centrifugation at top speed in a microcentrifuge. Without intending to be limited by theory, when swollen cells pass through the small pores of the filter the cell membrane is rapidly ruptured while leaving most nuclei and other organelles intact. Ruptured cell membrane with associated proteins, organdies, nuclei, and soluble cytosol proteins pass through the filter while aggregated cells and/or tissue debris are retained in the filter. Insoluble plasma membrane and organelles present in the supernatant may optionally be further separated from soluble cytosol proteins and nuclei by differential centrifugation. The whole procedure takes less than 30 minutes to complete. In another embodiment, isotonic buffer is used for isolation of organelles from cells and/or tissue with a cell wall, such as chloroplasts from plant tissues.

Membranes and organelles isolated using the methods described herein are in native forms which are suitable for applications such as protein electrophoresis, enzyme assays, immunoblotting, ELISA, immunoprecipitation and other assays. The methods presented herein provide the most rapid method currently available for isolating crude membranes and/or organelles from animal or plant samples. The unique features provided by this invention are simplicity, rapidity, reproducibility and it is user friendly. It is equally useful for single and multiple sample preparations with consistent results. It is the first use of a filter cartridge in a spin column format for membrane and/or organelle isolation.

Membrane refers to a membrane system, which refers broadly to plasma membrane with associated proteins, and other lipid bi-layer structures such as mitochondria, endoplasmic reticulum, Golgi apparatus, and, in a plant, plastids and chloroplasts.

"Crude membrane" refers to membrane with associated proteins that have been removed from its natural environment, e.g., it is in an environment different from that in which the membrane is naturally found. For instance, isolated membrane is cell membrane that is no longer part of an intact cell, and many of the polypeptides, nucleic acids, and other cellular material of its natural environment are no longer present. In one embodiment, "crude membrane" includes a preparation that is enriched for plasma membranes, organelle membranes (e.g., chloroplasts), endoplasmic reticulum membranes, and Golgi membranes. In one embodiment, "crude membrane" refers to a preparation where nuclei and/or nuclear membranes are reduced compared to a membrane preparation prepared by glass homogenizer or sonication or tissue blender.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. Drawing depicting an embodiment of a spin column with a hydrophobic porous filter (black area, 3) installed in accordance with the invention.

FIG. 2. Drawing depicting an embodiment of a collection tube having an optional hinged sealing cap 5.

FIG. 3. Drawing depicting an embodiment of the invention in which the spin column with hydrophobic filter medium 3 is placed inside a collection tube 6.

DETAILED DESCRIPTION OF ILLUSTRATIVE EMBODIMENTS

Figure 4:
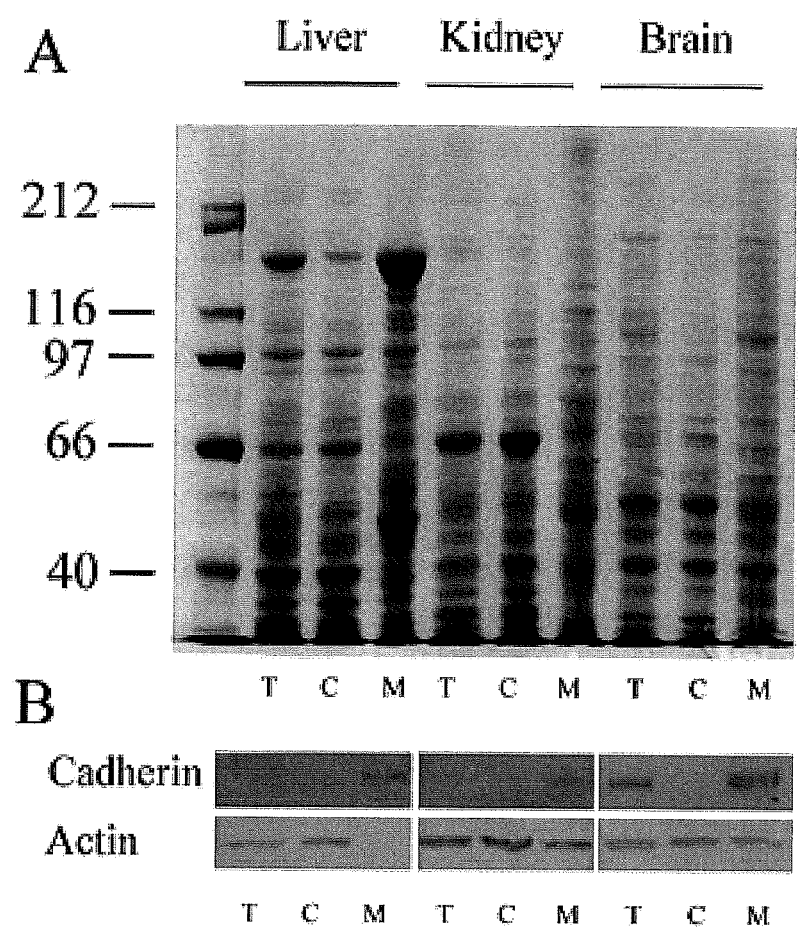
FIG. 4. A. SDS-PAGE protein profiles of crude membrane proteins from mouse tissues (mouse liver, kidney and brain). B. Proteins shown in A were transferred to a nitrocellulose membrane and probed with rabbit-anti mouse pan-cadherin (abeam, Cambridge, Mass.) and anti-actin by Western blotting. The specific proteins were visualized by a color metric substrate Opti-4CN (Bio-RAD). The signals of pan-cadherin (a 130 kda plasma membrane marker) were significantly enhanced in crude membrane fractions.

Provided herein are methods, reagents, and apparatus for rapidly extracting plasma membranes and/or organelles from cells and/or tissues, such as animal and/or plant cells and tissues. In one embodiment no detergent is used, thus the extracted membranes are in their native conformation, and the extracted membrane proteins are also in their native configuration. Examples of animal cells include, for instance, vertebrate cells including murine cells such as mouse and rat, human cells, and any other mammalian animal cell, and invertebrate cells including insect cells. Examples of plants include, for instance, those with green leaves (e.g., deciduous plants), including both monocots and dicots. The cells and/or tissue may be frozen. In one embodiment, the cells may be, for instance, primary cells (e.g., cells that have recently been removed from an animal or plant and are capable of limited growth in tissue culture medium), and cultured cells (e.g., cells that are capable of long term culture in tissue culture medium).

In one embodiment, the invention features a column apparatus (e.g. spin column device) for isolating crude membranes from tissues and/or cells. A positive force or a negative force may be applied to the apparatus. The apparatus includes a chamber 2 with a filtering medium 3 with defined pore size (FIG. 1) and a collection tube 6 with an optional hinged cap 5 (FIG. 2). The filtering medium may be hydrophobic. This apparatus is referred to as membrane extraction filter cartridge 7 (FIG. 3).

For animal samples, the cells are first incubated with a hypotonic buffer, and the cells are transferred to the chamber 2 of a membrane extraction cartridge using, for instance, a pipetting device. In those embodiments where fresh or frozen tissue is used, the tissue may be subjected to mechanical disruption before being filtered through the filtering medium, such as a hydrophobic filtering medium. For tissue samples with cells having a cell wall, e.g., plant samples, isotonic or hypotonic buffer may be used. In one embodiment, when a hydrophobic filter is used, the filter is not pre-wet with a solution in which the solvent is water. The mechanical disruption may be applying pressure to the sample inside or outside the filter cartridge with, for instance, a pipette tip, pestle or an appropriately sized rod to break up the sample.

Upon subjecting the apparatus to a positive or negative force, most of the cells are ruptured while passing through the filter. As a result, aggregated cells and/or tissue debris are retained on and within the filter medium 3, and disrupted cell membrane and/or organelles with associated proteins along with nuclei and soluble proteins pass through the filter medium 3 and are present in collection tube 6. The collection tube with flow through is first subjected to brief votexing to resuspend the cells, which may be in a pellet, followed by low speed centrifugation to remove intact nuclei and cell/tissue fragments that are small enough to pass the filter cartridge and big enough to be brought down by low speed centrifugation. Examples of low speed centrifugation include 400× to 600× for 1 to 3 minutes. The resulting supernatant, substantially free of nuclei and debris, is subjected to high speed centrifugation (10,000-12,000×g for 10-15 min) to separate insoluble membranes and organelles from soluble proteins in the supernatant. If desired, plasma membranes and other organelles can be further isolated from crude membranes by differential centrifugation such as sucrose density or gradient differential centrifugation, two phase partitioning, affinity purification, or other routine methods.

The methods described herein provide many advantages over available isolation methods in terms of speed, neatness, consistency, and yield. Most current membrane protein isolation procedures are tedious and time-consuming Many commercial membrane protein isolation procedures require more than one hour to complete. With methods disclosed herein, crude membrane can be isolated in less than 30 minutes. For instance, crude membranes may be isolated using the methods described herein in no greater than 30 minutes or no greater than 25 minutes. Isolation of crude membrane from tissue may take slightly longer, such as 1 to 3 minutes longer, due to the mechanical disruption of the tissue. The time of the process starts from re-suspending the cells in a buffer, such as a hypotonic buffer, and ends with the second centrifugation to obtain the crude membrane pellet. In comparison, current commercial membrane isolation kits often require around one hour to obtain crude membranes.

Due to the use of a membrane extraction filter cartridge, the quality of extracted membranes is consistent with high yield (at least 10 ug protein, up to, and in some embodiments greater than, 500 ug protein, from 1 million to 100 million cells or 1-50 mg tissue). This invention is useful for a broad range of sample size and is suitable for single and multiple preparations. In one embodiment, crude membranes can be isolated from as few as 1 million cells, for instance, at least 1 million, at least 5 million, at least 10 million, or at least 20 million. In one embodiment, the number of cells used is no greater than 50 million. In one embodiment, the amount of tissue used may be at least 1 mg, at least 5 mg, at least 10 mg, at least 15 mg, or at least 20 mg. In one embodiment, the amount of tissue used may be no greater than 50 mg, no greater than 40 mg, or no greater than 30 mg. The procedure can be easily scaled up to accommodate larger sample sizes. As a comparison, current commercial membrane isolation kits usually require a minimum starting cell number of greater than 5 million cells.

Also provided herein is a kit for isolating crude membranes from cells. The kit includes a membrane extraction filter cartridge in a suitable packaging material sufficient for at least one assay. Optionally, other reagents such as buffers and solutions needed to practice the invention are also included. Instructions for use of the packaged membrane extraction filter cartridge are also typically included.

As used herein, the phrase "packaging material" refers to one or more physical structures used to house the contents of the kit. The packaging material is constructed by routine methods, preferably to provide a sterile, contaminant-free environment. The packaging material has a label which indicates that the membrane extraction filter cartridge can be used for isolating membranes. In addition, the packaging material contains instructions indicating how the materials within the kit are employed to isolate membranes. As used herein, the term "package" refers to a solid matrix or material such as glass, plastic, paper, foil, and the like, capable of holding within fixed limits the components of the kit. Thus, for example, a package can be plastic containers used to contain membrane extraction filter cartridges and one or more buffers. "Instructions for use" typically include a tangible expression describing at least one assay method parameter, such as the relative amounts of reagent and sample to be admixed, maintenance time periods for reagent/sample admixtures, temperature, buffer conditions, and the like.

A. The Membrane Extraction Filter Cartridge

The present invention is best understood with the aid of the accompanying Figures. Referring to FIG. 1, the invention provides a membrane protein and organelle extraction apparatus including a spin column having a chamber 2 with a larger opening 1 and a smaller opening 4 having porous filtering medium 3 inserted for extracting membranes and retaining aggregated cells and/or tissue debris. In one embodiment, the average pore size of the filtering medium may be 30 however a pore size of 10, 20, 40, 50, and 60 µm may be used. The thickness of the filter medium may vary. One embodiment includes the use of a filter medium thickness of 6 mm which provides for retention of genomic material, aggregated cells and/or debris, and 2) a medium for rupturing the cells treated by hypotonic or isotonic buffer when passing through the filter. The thickness of the filter medium may be in a range of 0.5-20 mm in a spin column format, such as 0.5, 1, 2, 4, 6, 8, 10, 15, 18, and 20 mm. Examples of hydrophobic materials that may be used include, but are not limited to, polyethylene glycol, polyvinylidene fluoride, high density polyethylene, polypropylene, and the like. Though hydrophobic plastic filtering medium is the preferred material used in present invention, in some embodiments hydrophilic materials or hydrophilic materials with hydrophobic coatings may also be used. In addition to materials mentioned above, it may be possible to use other materials such as porcelain, rubber, foams and silicon filters. In one embodiment, the filter is made up of a network of non-directional filaments or particles. Without intending to be limited by theory, a useful filter is one that causes cells entering the filter to take a convoluted path through the filer, thereby subjecting the cells to mechanical stress resulting in rupturing of cell membranes within the filter. To extract crude membranes using the apparatus, the spin column with filtering medium 3 is placed in a collection tube 6 (FIG. 2) having an optional hinged cap 5 to form a complete membrane extraction filter cartridge 7 (FIG. 3).

B. Membrane Isolation Solutions

Many hypotonic solutions can be used in the methods disclosed herein. Examples of hypotonic solutions include, but are not limited to, Tris[hydroxylmethyl]-aminomethane hydrochloride (Tris-HCl, 10-100 mM, pH. 6-8), (4-(2-hydroxyethyl)-1-piperazineethanesulfonic acid (HEPES, 10-100 mM, pH 6-8) and trethanolamine (TEA, 1-10 mM, pH 6-8). Hypotonic solution refers to a solution that contains less solute compared to the cytoplasm of the cell. Other examples of a hypotonic solution useful herein include water, and dilute solutions of PBS, where a non-diluted solution may be 0.2 grams KCl, 0.2 grams $KH_2PO_4$, 8 grams NaCl, and 2.16 grams $Na_2HPO4*7H_2O$ in 1000 ml $H_2O$. The volume of hypotonic or isotonic solution used may be any volume sufficient to re-suspend the cells. In one embodiment, volumes of hypotonic or isotonic solution may be at least 100, at least 150, or at least 200 ul, and greater volumes are possible. In one embodiment, volumes of hypotonic or isotonic solution may be no greater than 500, no greater then 400, or no greater than 300 ul. In one embodiment, the hypotonic buffer does not result in rupture of a substantial percentage of cells. In one embodiment, the hypotonic buffer may result in rupture of at least 40%, at least 50%, at least 60%, at least 70%, at least 80%, or at least 90% of the cells. In one embodiment, the hypotonic buffer may result in rupture of no greater than 90%, no greater than 80%, no greater than 70%, no greater than 60%, no greater than 50%, or no greater than 40% of the cells.

Examples of isotonic solutions include the same solutions listed above, but at an osmolarity that is similar or identical to the cells. In one embodiment, an isotonic solution includes glass beads. The glass beads may be at a concentration of, for instance, 15%, 20%, or 25%. Any glass beads that act to break up cells and tissues, such as cells and tissues with cell walls, may be used in the methods disclosed herein. In one embodiment, the beads may have an average diameter of at least 40, at least 50, at least 60, or at least 70 um. In one embodiment, the beads may have an average diameter of no greater than 80, no greater than 70, no greater than 60, or no greater than 50 um. The glass beads may be crushed.

A membrane isolation solution may include compounds to inhibit protease activity. Examples of useful protease inhibitors include, but are not limited to, ethyenediamineletracetate (EDTA), leupetin and pepstatin A.

The present invention is illustrated by the following examples. It is to be understood that the particular examples, materials, amounts, and procedures are to be interpreted broadly in accordance with the scope and spirit of the invention as set forth herein.

Example 1

Isolation of Crude Membrane from Cultured Cells

Cultured mammalian cells were collected by low speed centrifugation (1500×g for 5 min) The cell pellet was washed once with cold phosphate-buffered saline (PBS) and the following steps were performed sequentially:
1. Resuspend the pellet in 0.5 ml ice-cold hypotonic Tris-HCl buffer with 5 mM MgCl2 pH 7.2.
2. Incubate the cell suspension on ice for 5 to 10 min. After incubation the cell suspension is transferred to a filter cartridge and centrifuged at 14,000 rpm in a microcentrifuge at 4° C. for 30 seconds.
3. Discard the filter and resuspend the pellet in collection tube by briefly vortexing. Centrifuge the tube at 3000 rpm for 1 min to remove most nuclei, un-ruptured cells and other debris. Carefully remove the supernatant without disturbing the pellet. Transfer the supernatant to a 1.5 ml microfuge tube and centrifuge the tube at 14,000 rpm at 4° C. for 15 min. The pellet contained isolated crude membranes.

Example 2

Isolation of Crude Membranes from Mouse Tissues

Fresh or frozen mouse tissue (20-40 mg) was placed in a filter cartridge. Two hundred microliters of cold hypotonic buffer (10 mM Tris-HCl, pH 7.5) was added to the tissue and the tissue was homogenized for 30 seconds with a flat end plastic rod. After homogenization 300 ul Tri-HCl buffer was added to the filter and the following steps were performed sequentially:
1. Centrifuged the filter cartridge at 14,000 rpm in a microcentrifuge at 4° C. for 30 seconds.
2. Discarded the filter and resuspended the pellet in collection tube by vortexing. Centrifuged the tube at 3000 rpm for 1 min to remove most nuclei, un-ruptured cells and tissue debris. Carefully removed the supernatant without disturbing the pellet. Transferred the supernatant to a 1.5 ml microfuge tube and centrifuged the tube at 14-16,000 rpm at 4° C. for 15 min. The pellet contained isolated crude membranes. FIG. 4 shows the results of proteins associated with membranes isolated from mouse tissues.

Example 3

Isolation of Chloroplasts from Plant Cells

Figure 5:
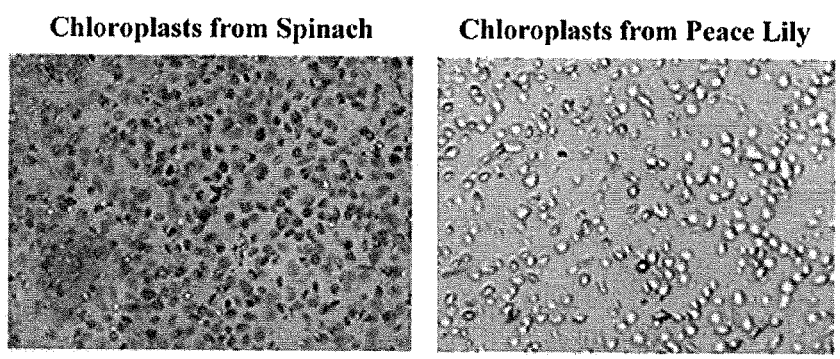
FIG. 5. Light microscope images of chloroplasts isolated from fresh leaves of Spinach (*Spinacia Oleracea*) and Peace Lily (*Spathiphyllum Cochlearispathum*). Magnification: 400×.

The following can be used for isolation of intact chloroplasts from 5-100 mg fresh plant tissue samples (leaves, seeds and soft stems etc.). If smaller or larger amounts of starting materials are used, the amount of buffers used may be adjusted proportionately.
1. Pre-chill buffers and the filter cartridge in collection tube on ice.
2. Approximately 5-100 mg fresh plant tissue were placed in the filter. Plant leaves were folded or rolled and inserted into the filter. The leaf was punched in the filter repeatedly with a pipette tip about 60 times to reduce the volume (for tissues less than 50 mg punching with the tip is not necessary). Seeds and soft stems were cut with a sharp blade into smaller pieces and placed in the filter cartridge(s).
3. Cold homogenization buffer (200 μl, 1×PBS with 20% glass bead, Crystal Mark Inc. Glendale, Calif.) was added to the filter (shake the bottle vigorously for a few seconds prior to pipetting). The tissue was ground with a plastic rod 50-60 times with twisting force.
4. The filter was capped and centrifuged in a microcentrifuge at 5,000 rpm at 4° C. for 1 min. The supernatant was removed and the pellet resuspended in 500 μl cold PBS by pipetting up and down or vortexing.
5. The mixture was centrifuged at 3,000 rpm for 2 min at 4° C., the supernatant removed and the pellet, was resuspended in 100 to 200 μl cold 1×PBS. The pellet contained isolated chloroplasts (see FIG. 5).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for isolating crude membrane from a cell comprising:

incubating animal cells in a hypotonic buffer to result in a mixture;

passing the mixture through a filter to rupture the cells and separate the mixture into retentate and filtrate, wherein the filtrate comprises crude membrane, nuclei, and soluble cytosolic proteins, wherein the filter is a hydrophobic filter that comprises a pore size from 20 um to 60 um and comprises a thickness of 2 millimeter (mm) to 20 mm, wherein the passing the mixture through the filter consists of a force selected from centrifugation and vacuum; and subjecting the filtrate to conditions suitable for separating crude membrane from the filtrate.

2. The method of claim 1 wherein the animal cells comprise cultured cells or cells from an animal tissue sample.

3. The method of claim 2 wherein the number of cells is as few as $1 \times 10^6$.

4. The method of claim 1 wherein the hydrophobic filter comprises a hydrophilic material covered with a hydrophobic coating.

5. The method of claim 1 wherein the incubating, passing, and subjecting are completed in no greater than 30 minutes.

6. The method of claim 1 wherein the animal cells have not been subjected to homogenization using a homogenizer, a blender, or a sonicator during the incubating.

* * * * *